(12) United States Patent
Folsom et al.

(10) Patent No.: US 12,076,244 B1
(45) Date of Patent: Sep. 3, 2024

(54) IMPLANTABLE CRANIAL CLOSURE DEVICE AND SYSTEM WITH A SONIC WINDOW AND ACCESS PORT

(71) Applicants: Aubrey Clinton Folsom, Pelham, AL (US); Kim Manwaring, Phoenix, AZ (US); Jotham Charles Manwaring, Washington, UT (US)

(72) Inventors: Aubrey Clinton Folsom, Pelham, AL (US); Kim Manwaring, Phoenix, AZ (US); Jotham Charles Manwaring, Washington, UT (US)

( * ) Notice: Subject to any disclaimer, the term of this patent is extended or adjusted under 35 U.S.C. 154(b) by 200 days.

(21) Appl. No.: 17/038,711

(22) Filed: Sep. 30, 2020

(51) Int. Cl.
| | |
|---|---|
| *A61F 2/28* | (2006.01) |
| *A61B 17/32* | (2006.01) |
| *A61B 90/00* | (2016.01) |
| *A61B 90/10* | (2016.01) |
| *A61F 2/30* | (2006.01) |

(Continued)

(52) U.S. Cl.
CPC .... *A61F 2/2875* (2013.01); *A61B 17/320068* (2013.01); *A61F 2/30749* (2013.01); *A61L 27/18* (2013.01); *A61M 37/0092* (2013.01); *A61M 39/0247* (2013.01); *A61N 7/00* (2013.01); *A61B 2017/320069* (2017.08); *A61B 2090/103* (2016.02); *A61B 2090/3925* (2016.02);

(Continued)

(58) Field of Classification Search
CPC .............. A61F 2/2875; A61F 2/30749; A61B 17/320068; A61B 2090/103; A61B 2090/3925; A61M 37/0092; A61M 39/0247; A61M 2039/025; A61N 7/00; A61N 2007/0026
See application file for complete search history.

(56) References Cited

U.S. PATENT DOCUMENTS 5,902,326 A * 5/1999 Lessar ................ A61B 5/14539
607/36
8,761,889 B2 * 6/2014 Wingeier ............... A61N 7/022
607/45

(Continued)

OTHER PUBLICATIONS

Roome, Christopher et al., "Chronic Cranial Window with Access Port for Repeated Cellular Manipulations, drug application, and electrophysiology", Frontier in Cellular Neroscience, Nov. 11, 2014; vol. 8, Article 379; pp. 1-8.

(Continued)

*Primary Examiner* — Theodore J Stigell
(74) *Attorney, Agent, or Firm* — Lanier Ford Shaver & Payne PC; Gerald M. Walsh (57) ABSTRACT

A sonic window implant having a border forming a ledge for attachment to the cranium. A sonic window, formed within the border, has a top exterior surface and a bottom interior surface. The top exterior surface and the bottom interior surface are parallel and curved. The implant is made of polyether ether ketone and is highly polished to allow transmission of ultrasound while the ledge is reflective of ultrasound for visualization of the border. Sutures in the sonic window tent the dura mater to the bottom interior surface. The sonic window has an access port for injection of therapeutics and application of instruments. The implant allows the use of ultrasound for imaging, diagnosis, and intraoperative treatment of the brain and allows ultrasound to be combined with pre-operative imaging from CT, MRI, PET, MEG, or EEG.

20 Claims, 6 Drawing Sheets

(51) Int. Cl.
*A61L 27/18* (2006.01)
*A61M 37/00* (2006.01)
*A61M 39/02* (2006.01)
*A61N 7/00* (2006.01)

(52) U.S. Cl.
CPC .............. *A61M 2039/025* (2013.01); *A61N 2007/0026* (2013.01)

(56) References Cited

U.S. PATENT DOCUMENTS

| | | |
|---|---|---|
| 9,044,195 B2 | 6/2015 | Manwaring et al. |
| 2007/0038100 A1* | 2/2007 | Nita ................. A61M 37/0092 600/439 |
| 2008/0208236 A1* | 8/2008 | Hobbs ............... A61M 39/0208 606/186 |
| 2010/0168871 A1* | 7/2010 | Liao ..................... A61F 2/2875 623/23.72 |
| 2014/0330123 A1* | 11/2014 | Manwaring .......... A61B 8/4444 600/443 |
| 2019/0069927 A1* | 3/2019 | Baxter, III ........... A61N 1/0529 |
| 2020/0138580 A1* | 5/2020 | Carpentier ............... A61N 7/00 |
| 2020/0197180 A1* | 6/2020 | Christopher .......... A61B 5/4064 |
| 2020/0375745 A1* | 12/2020 | Sampath ............... A61F 2/2875 |
| 2021/0121088 A1* | 4/2021 | Christopher ......... A61B 5/0022 |

OTHER PUBLICATIONS

Bonda et al., "The Recent Revolution in the Design and Manufacture of Cranial Implants: Modern Advancements and Future Directions", Neurosurgery, Nov. 2015; 77(5); pp. 814-824.

\* cited by examiner

IMPLANTABLE CRANIAL CLOSURE DEVICE AND SYSTEM WITH A SONIC WINDOW AND ACCESS PORT

FIELD OF THE INVENTION

This invention relates to cranial closure devices with windows and, more particularly, to sonic window systems that allow the transmission of ultrasound for imaging, diagnosis, and treatment of disorders of the brain.

BACKGROUND OF THE INVENTION

Ultrasound is defined by the American National Standards Institute as "sound at frequencies greater than 20 kHz". In air at atmospheric pressure, ultrasonic waves have wavelengths of 1.9 cm or less. Transfontanel ultrasound is known to be useful in infants before the anterior fontanel closes to form the cranial bregma. Diagnostic and therapeutic ultrasound energy is severely impeded by the cranium so the use of ultrasound beyond the typical closure age of about 18 months has not been practical. However, re-creation of the anterior fontanel by a surgical procedure can re-enable the use of ultrasound modalities with the well-known benefits of real time imaging with nonionizing energy, in contrast to x-ray or the comparatively costly or encumbering imaging modalities of computed tomography (CT) and magnetic resonance imaging (MRI). Yet further, ultrasound as an imaging methodology is easily deployed remotely to rural clinics or even homes with internet-enabled interpretation. However, a re-created anterior fontanel or any open cranial defect makes the brain vulnerable to the loss of cranial protection from trauma and may make the head appearance unattractive for loss of the conforming shape afforded by bone. U.S. Pat. No. 9,044,195 indicates that an implantable sonic window can restore mechanical integrity to the cranium yet transmit ultrasound which may significantly improve diagnostic and therapeutic flexibility and options, while re-establishing cranial safety. U.S. Pat. No. 9,044,195 is incorporated herein by reference.

Marginal quality ultrasound for Doppler ultrasonography of the vasculature of the brain or for imaging the temporal lobe through intact, thin cranium can be substantially enhanced by replacement of the cranium with a cranial window implant. The cranial window can be used as an ultrasound "window" if the implant material is highly ultrasound lucent or transmissible. Doppler ultrasound enables visualization and quantification of blood flow in tissues. In the instance of staged treatment or surveillance of efficacy of treatment of vascular malformations, such an appropriately positioned cranial window could provide useful long-term assessment of disease status.

More recently, therapeutic ultrasound energy has been recognized to have potential utility in neuromodulation (alteration or restoration of brain circuit functionality). Further, chemotherapy by focused ablation or by opening the blood-brain barrier allows tissue penetration of drugs. High intensity focused ultrasound, low intensity ultrasound, and various pulsed modes for tissue activation or suppression, for example to treat clinical depression or seizure control, respectively, may be enabled by an appropriately placed cranial window into the cranium.

U.S. Pat. No. 9,044,195 discloses polymeric material, such as polyethylene, polystyrene, acrylic, or poly(methyl methacrylate, PMMA) to be biologically compatible, sufficiently mechanically strong, and ultrasound lucent to enable transmitting ultrasonic waves into the brain. Polytetrafluoroethylene (PTFE), also known by the proprietary name of Teflon, more severely attenuates ultrasound transmission. In contrast, silicone (polysiloxane) severely attenuates ultrasound energy, thus limiting its usefulness for transmitting ultrasonic waves into the brain. Similarly, metallic plating or mesh severely reflects ultrasound energy. These materials are widely used in the body. For example, ultra-high molecular weight polyethylene has been used successfully in joint replacement and polyethylene as implant mesh for hernias and as suture. These polymers have been shown to have sufficiently low reactive characteristics to integrate or heal without excessive scar or adhesion and with minimal risk as a nidus for infection. In addition, implants of these polymers can be modified on the surgical field for optimal edge matching or to achieve acceptable contour. They can be secured to the cranium with methods of press fit or the use of sutures or plates and screws of both permanent metal or plastic types or absorbable types. For example, burr hole covers made of silicone are commonly positioned with simple press-fit into a cranial defect and snugly held by the healing process of fibrous encasement. Alternatively, less precise shapes can be secured by bridging gaps between the materials with titanium plates. Even glue adhesives can secure the implant. More porous versions of implant material at margins can engage the healing bone edge, but these materials will not effectively transmit ultrasound energy.

All surface areas of the cranium can now be modeled from imaging data to create an individualized polymer implant out of various materials. Some regions of the cranium change in curvature minimally such that certain generic implants can be employed across most patient head shapes. Of particular clinical usefulness is a generic implant which affords standardized image slice appearance and comparison as conventionally used in both CT and MRI scanning. For example, replacement of the bregma following re-creation of the anterior fontanel in humans enables standard ultrasound across a wide range of ages by allowing the coronal, sagittal, and axial viewing angles as well as insonation of cerebral arterial and venous flow using Doppler imaging. The curve of the cranium in the bregma region, situated well behind the hairline, changes little across male and female, adolescent to elderly, and various races or ethnicities. Therefore, such generic sonic windows from ultrasonically lucent polymers can be adapted at surgery to the patient without pre-ordering a customized fit. Similarly, a cranial sonic window over the frontal cranium just below the hairline can be broadly adapted, but with the greater benefit in that there is no hair in this region to obscure ultrasound or which would require shaving or excess application of ultrasound gel to improve transmission. The frontal cranium just below the hairline is especially useful as it closely aligns with standard axial images of the brain as obtained in CT and MRI imaging. This location facilitates easy orientation for the clinician in long term sequential surveillance for common chronic conditions such as hydrocephalus and arachnoid cysts as well as observation of certain lesions or resection cavities in brain tissue.

All polymer implants can be expected to increase risk for infection. While generally considered an acceptably low risk in their current usage in various parts of the body, any methods which can decrease such risk are attractive to the clinician. Although certain microscopic level surfaces have been shown to be antibiotic, these generally will reflect ultrasound energy and are less desirable.

In view of the feasibility of applying ultrasound to the brain through an implanted sonic window, it is desirable to improve the fixation of the implant window to the skull and dura mater, increase the transmission of ultrasonic energy through the sonic window, facilitate the use of templates to create a window of precise dimension and shape, detect blood flow and spinal fluid, use intraoperative ultrasound in intraoperative localization and delineation of lesions, and plan various stages of tumor resection, in conjunction with MRI and CT scanning.

SUMMARY OF THE INVENTION

The present invention is a sonic window implant device which has a border forming a ledge and a sonic window within the border. The sonic window is transmissible to ultrasound and has a top exterior surface and a bottom interior surface. An extending portion of the sonic window extends below the ledge. The top exterior surface and the bottom interior surface are parallel and curved to conform to the shape of a cranium. The ledge is reflective of ultrasound for visualization of the border. The sonic window implant is made, preferably, of polyether ether ketone and the top exterior surface and the bottom interior surface are polished to at least a 16-micron root mean square. The sonic window may have an access port and the ledge may contain indicia readable through ultrasound. The top exterior surface and the bottom interior surface may be coated with polytetrafluoro ethylene to inhibit adhesion of the sonic window to tissue. The ledge has one or more holes constructed to attach the sonic window implant device to a cranium with screws. The sonic window has one or more pairs of holes with sutures constructed to tent dura mater upward to the bottom interior surface of the sonic window. The ledge may be attached with screws to a recessed bone ledge in an opening in the cranium and may be attached to dura mater with sutures.

The sonic window may have one or more bridging plates attaching the sonic window implant device to a cranium. A template of the sonic window may be used for creating an opening in a cranium for implanting the sonic window implant device.

The sonic window implant device provides a system for treating the cortex or subjacent tissue of the brain white matter or nuclei with ultrasound when the sonic window implant device is implanted in an opening in a cranium over an area of the cortex to be treated. Ultrasound through the sonic window is used to ablate target tissue, to open the blood brain barrier for chemotherapy, and/or to perform neuromodulation. The ultrasound can be combined with pre-procedure imaging from CT, MRI, positron emission tomography (PET), magnetoencephalogry (MEG), or electroencephaly (EEG) data to localize a target tissue and/or compensate for tissue movement. The access port in the sonic window may be used for injecting therapeutic substances or for insertion of surgical instruments.

Implanting the sonic window implant device includes forming a recessed bone ledge at a top of the cranial opening to engage the ledge of the sonic window implant device. The sonic window implant device is inserted into the cranial opening to the level of the dura mater and the ledge of the sonic window implant device is fastened to the recessed bone ledge. Any gap that forms between the bottom interior surface of the sonic window and the dura mater is filled with an ultrasound conductive liquid or gel. A suture is passed down through a first hole in the ledge of the sonic window implant device, through the dura mater, up through a second hole in the ledge of the sonic window adjacent the first hole, and the dura mater is tented to the bottom interior surface of the sonic window with the suture.

An advantage of the present invention is a sonic window implant that can be fixed to a recessed ledge in an opening in the cranium.

Another advantage is a sonic window implant that can tent the dura mater against the bottom interior surface of the sonic window to prevent a gap from forming therebetween.

Another advantage is a sonic window implant made of polyether ether ketone that can be highly polished to allow and optimize the transmission of ultrasound through the sonic window.

Another advantage is a sonic window implant having a border reflective to sound and having indicia for identification.

Another advantage is a sonic window implant that is curved to conform to the curvature of the cranium.

Another advantage is a sonic window implant that has a port in the sonic window for injection of therapeutic agents and for applying instruments.

Another advantage is a sonic window implant that allows the use of ultrasound for imaging, diagnosis, and intraoperative treatment of the tissues of the brain.

Another advantage is a sonic window implant that allows ultrasound to be combined with pre-operative imaging from CT, MRI, PET, MEG, and EEG.

DETAILED DESCRIPTION OF THE INVENTION

While the following description details the preferred embodiments of the present invention, it is to be understood that the invention is not limited in its application to the details of arrangement of the parts or steps of the methods illustrated in the accompanying figures, since the invention is capable of other embodiments and of being practiced in various ways.

A sonic window implant polymer, to be highly transmissive of ultrasound energy (ultrasonic waves), must have a polished and optimally ultra-smooth surface on both a top exterior surface adjacent to scalp tissues and a bottom interior surface adjacent to the dura mater. A scratching or scoring of those surfaces reflects ultrasound energy and particularly obscures the nearfield millimeters of subjacent brain to both diagnostic and targetable therapeutic ultrasound. Conventional milled or 3D printed polyether ether ketone (PEEK) with its rougher surfaces, for example, can significantly impede ultrasound penetration. However, PEEK has been demonstrated for many years to be a useful cranial substitute after complex destructive trauma to the cranium or for reconstruction of the cranium post decompressive craniectomy. It can be customized to the individual cranial contour of a portion of the cranium which requires replacement using both modification on the bench of preformed pieces or made as an exactly fitting implant from CT scan data. Further, such polymers have been shown to have sufficiently low reactive characteristics to integrate or heal without excessive scar or adhesion and with minimal risk as a nidus for infection. Yet further, such implants can be modified on the surgical field for optimal edge matching or to achieve acceptable contour. They can be secured to the cranium with methods of press fit or with the use of sutures or plates and screws of both permanent metal or plastic types or absorbable types.

Any surgical milling for optimal fit on the surgical field by burring in the region of the ultrasound window can deteriorate usefulness of the implant. While some lower melting temperature polymers like polypropylene and polyethylene can be poured in the manufacturing process with a resultant mirror-like finish, PEEK is generally milled, or 3D printed. Intrinsic laminations or surface roughness are readily apparent as limitations to the diagnostic and therapeutic applications. However, if PEEK sonic implants are highly polished, they transmit ultrasound adequately.

In the clinical setting it is highly desirable to have markers on the implanted sonic window which allow for ready recognition of borders and optimal positioning of the ultrasound transducer which is placed on the scalp. Just as a scored surface of any of the aforementioned polymers severely reflects ultrasound energy and attenuates transmission, a sonic window can be modified by a scored border to create an ultrasound appearance of the frame of a picture window. Such an orientation marker can be milled or etched on the peripheral margin of the implant, such as a hatched signature. Similarly, data of implant design, manufacture, and time stamp can be included here and interrogated by nearfield ultrasound. Of course, there should be no such markings in the region of the sonic window centrally. Various shapes such as circular or square windows or irregularly shaped windows can be made in custom fashion which include such peripheral identification by ultrasound means.

An implant, in order to enable sonic transmission, must enable direct contact to the subjacent dura mater or have a space which can be filled with ultrasound conductive fluid such as saline or conductive gel. For example, a gap between the inner mirror surface and dura which entraps air at time of placement in surgery will not be useful for ultrasound in either diagnostic or therapeutic modalities due to the severe attenuation. Therefore, means for snugging the dura to the bottom interior surface of the implant with peripheral sutures is desirable. Eventually, even without such snugging, fibrous healing will adhere the dura to that surface, but the timeframe for that to occur can be weeks to months. The window design and its surgical insertion must address this issue if immediate use is contemplated. This issue can be resolved by peripheral dural tack up sutures and the use of ultrasound conductive gel or saline. A central tack up suture can be employed, but it will necessitate creation of an ultrasound-obscuring artifact. Yet alternatively, the sonic window implant can be placed into an ultrathin sac of polymer prior to surgical seating which material conveys the surface property of nonsticking. The ultrathin sac can be fabricated of PTFE (Teflon). Further, the sac can have antibiotic properties to diminish the risk of infection post implantation.

To simplify surgical placement and minimize time under anesthesia, a sonic window template can be employed to inform the surgeon of precise cuts to conform and secure the sonic window. The rectangular shaped window is generally the most easily adapted due to the typical rectangular shape of the ultrasound transducer applied over the scalp. The template is a curved, rectangular shape identical to the proposed implant and allows tracing of the cranium with a surgical ink or monopolar desiccation line to enable a precise burr hole to the level of the dura and a rectangular cut of full thickness bone with conventional high-speed routing bits. Yet further, the template indicates a ledge as a border to the sonic window which allows the implant to be lowered to the level of the cranium to minimize any marginal burring or shaping needed to conform the implant to the patient's cranial contour. The template also indicates the locations of peripheral small holes on the margin of the ledge to tack the dura snugly to a bottom interior surface of the implant.

Figure 1A:
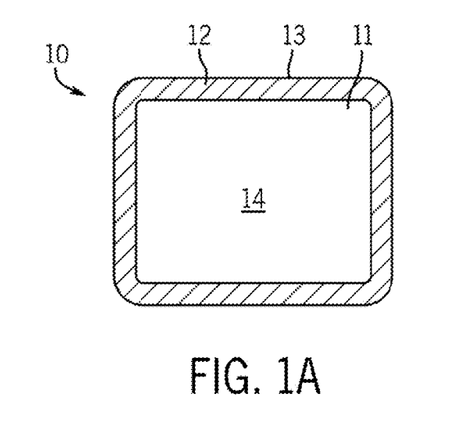
FIG. 1A shows a view of a top exterior surface of a sonic window implant of the present invention.
Figure 1B:
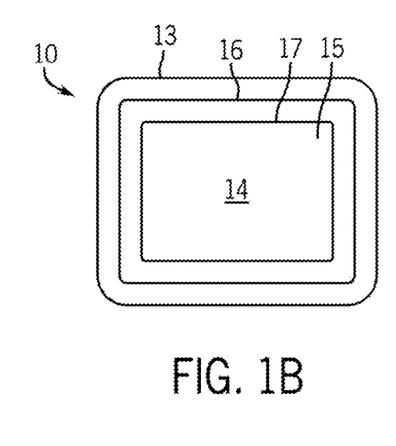
FIG. 1B shows a view of a bottom interior surface of the sonic window implant.
Figure 1C:
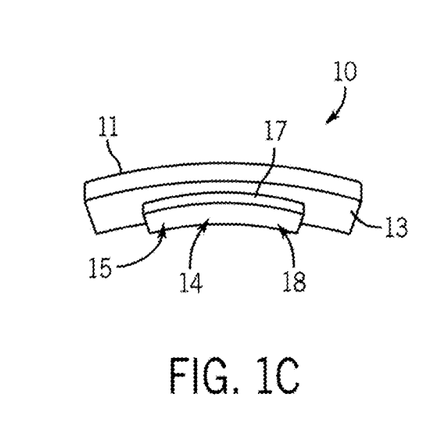
FIG. 1C shows a bottom perspective view of the sonic window implant.

FIG. 1A shows a view of a top exterior surface 11 of a sonic window implant 10 of the present invention. The implant 10 is, preferably, rectangular and has a hatched border 12 which forms a ledge 13. A sonic widow 14 is contained within the border 12. FIG. 1B shows a view of a bottom interior surface 15 of the sonic window implant 10. A recessed track strip 16 is formed on the bottom interior surface 15 of the ledge 13 around the edges 17 of the sonic window 14 as an adhesive distribution strip, if desired. FIG. 1C shows a bottom perspective view of the sonic window implant 10. It can be seen that there is an extending portion 18 of the sonic window 14 that extends below the ledge 13. It can be seen in FIG. 1C that the top exterior surface 11 and the bottom interior surface 15 are parallel and curved, providing a contour curvature of polished parallel planes to the sonic window 14.

The sonic implant of FIGS. 1A-C provides a sonic window designed for placement at the bregma of the cranium or at the anterior hairline in the midline directly over the sagittal sinus to afford standard ultrasonic imaging. The curved feature allows general adaptation in these locations over a wide range of ages in adults. The exterior and interior surfaces are parallel to enable ultrasound transmission without distortion. The width and length of the sonic window are, preferably, 2.5×3.5 cm, respectively. The width and length of the implant including the ledges are, preferably, 3.5×4.5 cm, respectively. The thickness of the sonic window is, preferably, 4 mm. The hatched border is, preferably, 5 mm width.

The longitudinal curve radius and the width curve radius may be manufactured in various radii to fit individual patients. Custom implants may be provided to cover unique patient situations. The top exterior surface and the bottom interior surface of the sonic window are highly polished. The roughness index measurement is described by the root mean square, (RMS) and is 16 RMS or smoother. RMS is calculated as the Root Mean Square of a surface's measured microscopic peaks and valleys, measured in microns.

A highly polished surface finish on a PEEK plastic part may be obtained, for example, by positioning a PEEK plastic part slightly tilted, at an angle of 25 to 45 degrees, preferably 30 degrees, in a 5 axis CNC machining center during a machining process. The cutter of the CNC machine is, preferably, a ball nose end mill so that by slightly tilting the plastic part the cutter does not present the center of the cutter to the surface of the plastic part. This orientation of the plastic part enables a clean cutting path on the surface of the plastic part. The CNC machine is programed for the cutter to take small successive cuts in the plastic part that leave a very tiny ridge between passes of the cutter. Filtered air is applied on the cutting tool to keep the cutting tool cool and to remove chips of material. The filtered air must be clean and free of foreign material, especially oil. The resulting surface on the plastic part is less than 16 RMS because the machine spindle of the CNC machine is very precise.

There are polishing techniques that can produce a finish similar to that described above using abrasive powders, such as diamond particles or aluminum oxide granules in a carrier fluid or paste. However, these polishing techniques can cause the abrasive powders to embed in the surface of the plastic part and entrap the carrier fluid or paste. The use of coolants and lubricants other than filtered air is considered a contamination. The sonic implant produced from the plastic part must be certified as free of these extraneous materials because the sonic implant comes into contact with neural tissue. Machining the surface as described above is the best way to avoid contamination from abrasives, carriers for abrasives, coolants, and lubricants.

The sonic window implant in FIGS. 1A-1C is a generic implant, in contrast to a customized implant, which may have an irregular shape. The rectangular shape of the sonic window implant facilitates positioning the implant into the cranium and matches the typical rectangular shape of the ultrasound transducer. While the sonic window implant may be fabricated of polyethylene, polypropylene, or PEEK as biologically compatible materials with long experience of use in the body, PEEK has specifically been used for many years as a cranioplasty material.

There are two locations in the cranium with little change in curvature which are broadly applicable to standardized ultrasonic (US) imaging, the bregma and the midline anterior hairline. For example, a young child with complex hydrocephalus and a fused or closed anterior fontanel can benefit from noninvasive ultrasound by the simple surgical procedure of re-creation of the anterior fontanel using the sonic window implant of FIGS. 1A-C constructed, preferably, with PEEK. The ledges of the implant overlap the cranium, preventing dislodgement and the recessed track strip facilitates the spread of a glue adhesive, should that method be employed at surgery.

The implant can be surgically milled in the field to taper a desired contour. The implant curvature can also be adapted to the anterior hairline across most head shapes and range of ages. The sonic window is ideally 4 mm thick due to generic adaptation to the cranium thickness and contact to the dura but can be as thin as 1 mm and as thick as 10 mm in other locations without deterioration of image quality. The curve of the two parallel polished planes of the sonic window minimize distortion of ultrasound and optimize a near field to deep field range, from subjacent dura up to 12 cm into the brain.

The ultrasonic methods of coronal, sagittal, and axial orientation through this implant are enabled with conventional ultrasound equipment found in hospital radiology departments. In addition, new portable point of service ultrasound transducers which plug into smartphones or smart tablets can be used in an office or home. The hatched border is highly reflective of ultrasound to facilitate location of the polished window when the clinician or technician applies an ultrasound transducer over the scalp.

The top exterior and bottom interior surfaces of the sonic window implant may be coated with a thin layer of PTFE (Teflon) to minimize tissue adhesion in the healing process, enabling subsequent removal of the implant. The PTFE coating is transparent and less than 0.1 mm thickness. This thin PTFE coating has minimal impact on ultrasound reflectivity compared to the undesirable interference of a full thickness PTFE sonic window implant. However, the slick surface of the PTFE coating reacts with the dura and pericranium by development of an ultra-smooth translucent adhesion during the healing process which releases readily by light surgical traction. Maintaining the conditions of surgical surveillance afforded by the sonic window may require re-operation on occasion, for example recurrent neoplasm on the wall of a resection cavity in the brain. Similarly, infection of the implant may require its removal. Since the implant can lie over a major dural sinus or other critical margins, easy removability and replacement of the sonic window implant are clinical benefits.

Figure 2A:
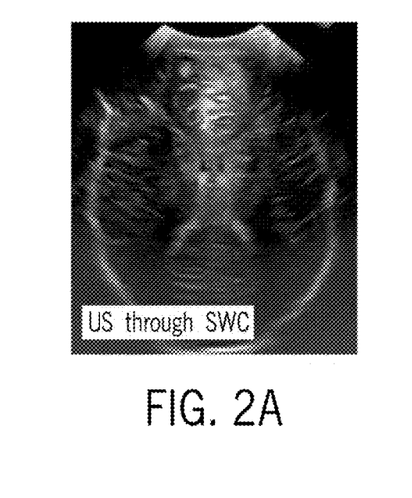
FIG. 2A shows sequentially obtained axial renderings of the brain by ultrasound through a sonic window cranioplasty implant device positioned directly beneath the hairline over the midline cranium.
Figure 2B:
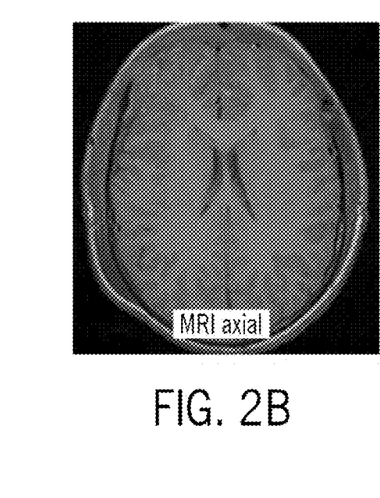
FIG. 2B shows sequentially obtained axial renderings of the brain by MRI corresponding to the same location as the sonic window cranioplasty implant positioned directly beneath the hairline over the midline cranium.
Figure 2C:
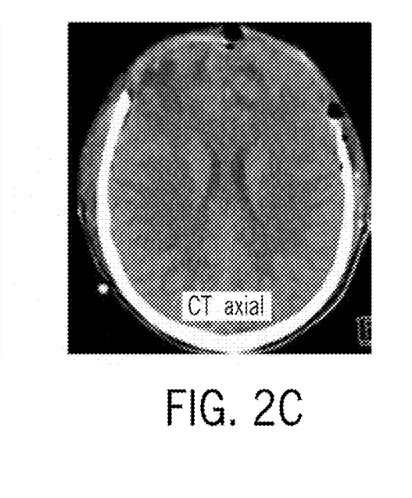
FIG. 2C shows sequentially obtained axial renderings of the brain by CT corresponding to the same location as the through the sonic window cranioplasty implant positioned directly beneath the hairline over the midline cranium.

FIGS. 2A-C show sequentially obtained axial renderings of the brain by ultrasound, MRI, and CT through a sonic window cranioplasty (SWC) implant positioned directly beneath the hairline over the midline cranium. Clinicians and radiologists find an implant location below the anterior hairline attractive. There is no hair overlying the forehead scalp skin, so the use of ultrasound conductive gel to enable imaging is minimal and the reflection artifact from matted hair caused by thick gel is avoided. Most particularly, the axial image plane of ultrasound matches closely the plane which is used in standard CT imaging and MRI imaging of the brain, as illustrated in FIGS. 2A-2C. Ultrasound transducers are adjustable for frequency and power to allow the full depth inside the head to be assessable. As ultrasound is excellent for brain tissue-fluid interface, this implant location enables long term surveillance of conditions such as hydrocephalus, arachnoid cyst, resection cavities, and chronic subdural effusions. Ultrasound is also very sensitive to ischemic change where margins of tissue injury and sufficiency of vascular perfusion are of clinical importance. Similarly, the Doppler adaptation of ultrasound allows imaging of the principle vasculature beyond what can be obtained through the thin temporal bones.

Figure 3:
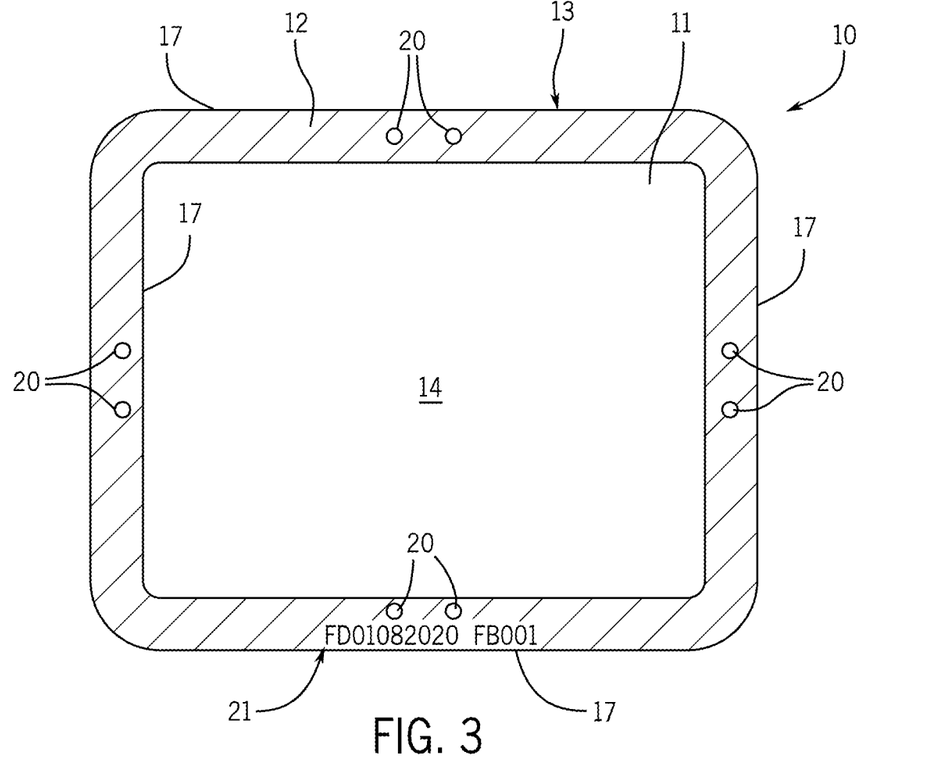
FIG. 3 shows a view of a top exterior surface of a sonic window implant having tack up holes in a hatched peripheral border.

FIG. 3 shows a view of a top exterior surface 11 of a sonic window implant 10 having tack up holes 20 in the hatched peripheral border 12. The implantable, rectangular, sonic window 14 has a highly polished top exterior surface 11 ultrasound transmission area. The hatched peripheral border 12 is highly reflective of ultrasound. The border hatching 21 also includes indicia such as the serial number of manufactures for identification and tracking purposes. The hatched peripheral border 12 can have a pattern of high roughness, irregular scoring, or a regular scoring. Apart from high ultrasound reflectivity for localization purposes, the hatched peripheral border 12 also is a zone of a lateral ledge 13 for positioning on subjacent cranium.

The sonic window implant 10 can be surgically milled or resected to optimize a fit of the sonic window 14 into the cranium. Yet further, data of manufacture can be milled into the border as shown here. This data can be read through high frequency, near field ultrasound to inform such aspects as design type and date of manufacture or even customized information.

Figure 4:
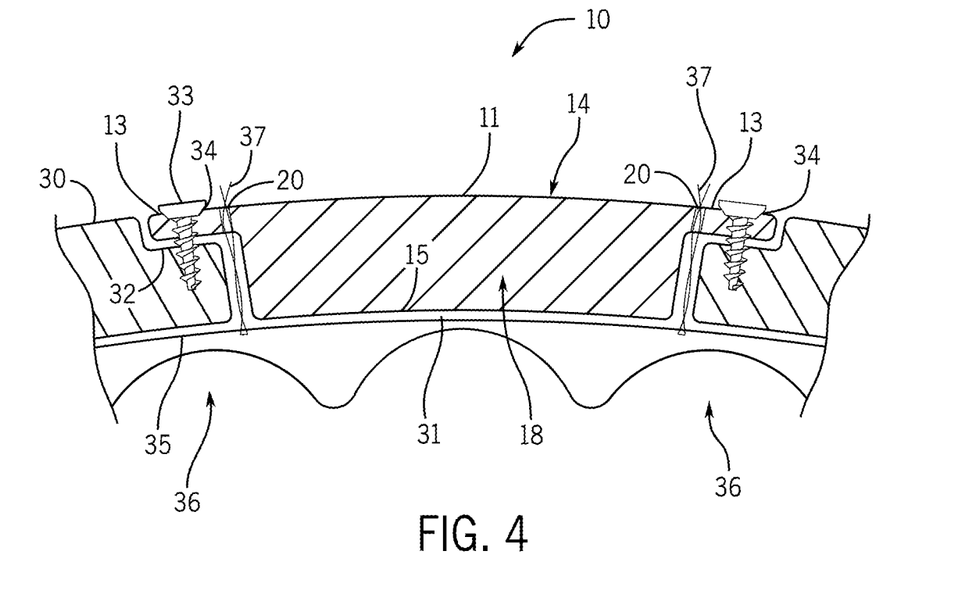
FIG. 4 shows a cross section view of the cranial sonic window implant implanted in the cranium through a surgical opening.

FIG. 4 shows a cross section view of the cranial sonic window implant 10 implanted in the cranium 30 through a surgical opening 31. A recessed bone ledge 32 may be formed at the top of the opening 31 for engaging a ledge 13 of the sonic widow implant 10. An extending portion 18 of the sonic window 14 extends into the surgical opening 31. The bottom interior surface 15 of the extending portion 18 engages the dura 35 located on the surface of the cortex 36. The bottom interior surface 15 is, preferably, polished. The position of tack up holes 20 allows tenting of the dura 35 to the bottom interior surface 15. It is ideal to efface the polished bottom interior surface 15 onto the dura 35 and to tent the dura 15 upward against the bottom interior surface 15 using peripheral sutures 37, preferably 4-0 Neurolon. The ledge 13 of the sonic window implant 10 is positioned in the recessed bone ledge 32 and can be attached thereto with tack down screws 33 through screw holes 34 into the ledge 13.

It is desirable to achieve dural contact of the bottom interior surface of the sonic window at the time of placement. While a generic window has a thickness of 4 mm between the parallel, polished top exterior surface and bottom interior surface, there is much surgical flexibility to achieve this contact if the adjacent cranium is thicker or even irregular in thickness. For example, the ledges resting on adjacent cranium can be recessed deeper by creating a recess in the outer bony cranium. If the outer bony cranium is thin, a tolerance up to 2 mm range of indentation upon the dura is reasonable. Any air gap between the dura and bottom interior polished surface will make the sonic window unusable, due to high ultrasound reflection, until the air is absorbed. Absorption may require weeks of healing time post-surgery. The gap can be eliminated at surgery by injecting saline or sterile ultrasound-conductive gel into the gap. The sonic window can then be immediately used. The saline or conductive gel is absorbed, leaving any dura-implant gap closed. A well fitted window in the cranium will be sufficiently secured by wall contact, the ledge preventing downward displacement, and dural tenting sutures being knotted on the top exterior surface of the sonic window as shown in FIG. 4. Normal scalp healing with adhesion of the pericranium further secures the stability of the sonic window implant. The tack-down screws are made, preferably, of titanium and are used, if desired, at the lateral margins of the ledge for fastening the ledge to subjacent cranium. The use of tack-down screws would be essential if the sonic window has not been secured by press-fit dimensions and dural tack up.

Figure 5:
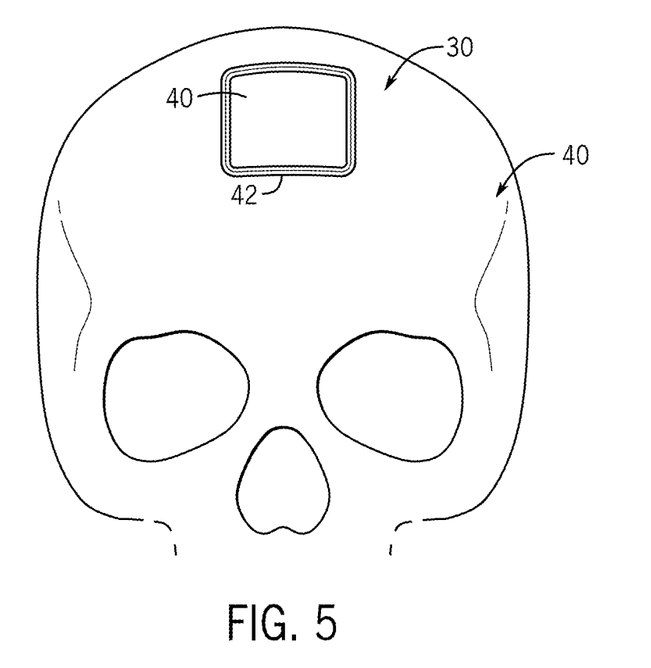
FIG. 5 illustrates the use of a cutting template for tracing an outline of an opening for a sonic window implant on the cranium of a skull.

FIG. 5 illustrates the use of a cutting template 40 for tracing an outline of an opening for a sonic window implant on the cranium 30 of a skull 41. The template is placed on the cranium and a cutting line 41 is traced around the template. The cutting line has the exact dimensions of the highly polished region of the sonic window to be implanted in the cranium. A surgeon selects an optimal location, for example bregma or anterior hairline, and traces the template with a surgical pen or with a monopolar desiccation method to show the cut line for snug fitting of the sonic window. The template can be made of tracing paper, metal, or plastic, but must be held immobile while the tracing step is undertaken.

Figure 6:
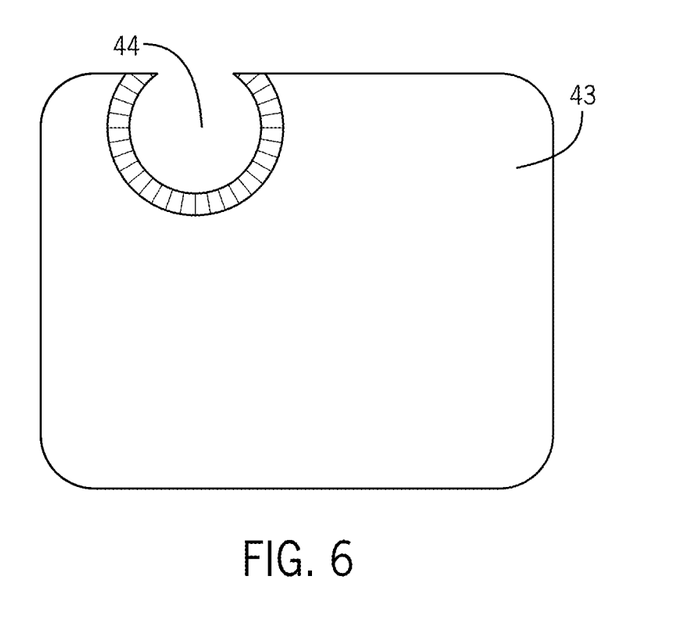
FIG. 6 shows a top view of a resected cranium obtained using a drill to drill a burr hole in the cranium and then a routing saw to cut along a traced cutting line on the cranium to the level of the dura.

FIG. 6 illustrates an example of a resected cranium 43 obtained using a drill to drill a burr hole 44 in the cranium and then a routing saw to cut along a traced cutting line on the cranium to the level of the dura. The routing saw can follow the traced cutting line precisely. The dimensions of the removed bone are identical to the dimensions of a sonic window to be implanted. Ledges on the sonic window implant will seat on adjacent cranium. Ledge width is ideally in the range of 5 mm and the ledges, preferably, contain an overlying hatched region for high ultrasound reflectivity.

Figure 7A:
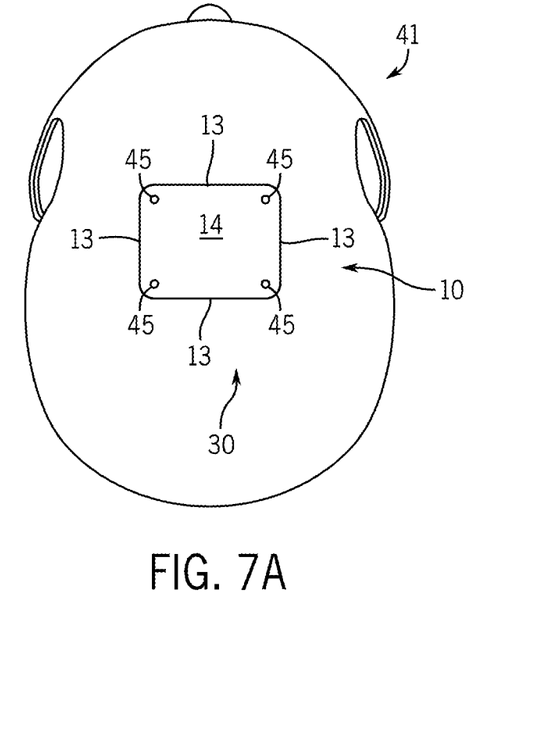
FIG. 7A shows a top view of a cranial sonic window implant which has been secured into the cranium with four titanium screws through drill holes at corners of a sonic window implant.

FIG. 7A shows a cranial sonic window implant 10 which has been secured into the cranium 30 with four titanium screws 45 through drill holes at corners of the sonic window implant 10. Minimal securing of the sonic window implant 10 is acceptable since the sonic window implant 10 includes a conforming overlapping ledge 13 which seats into a recessed margin of the opening of the cranium. The opening of the cranium can be recessed by burring a margin of the cranium to a desired level before seating the sonic window to the level of the dura and securing the ledge 13 with the screws 45.

Figure 7B:
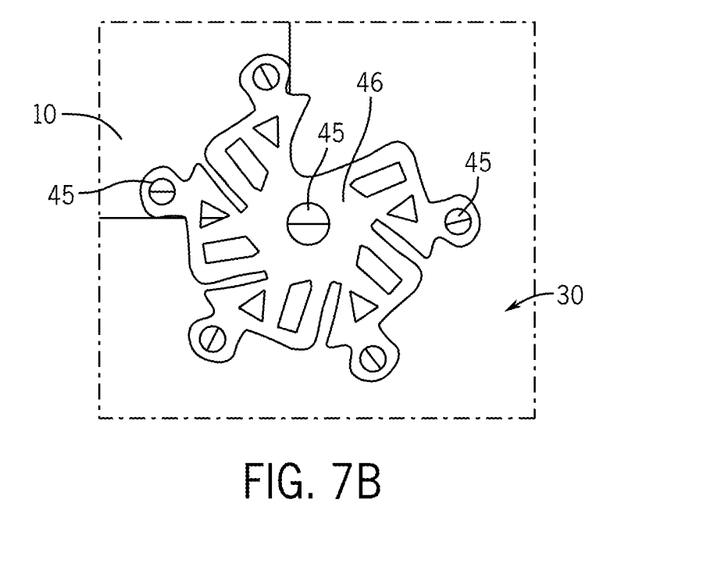
FIG. 7B shows a top view of a titanium cranial fixation plate attached to a corner of a sonic window implant and to a cranium with a plurality of titanium screws.

FIG. 7B shows a titanium cranial fixation plate 46 attached to a corner of sonic window implant 10 and to a cranium 30 with a plurality of titanium screws 45. This technique can be employed to further stabilize the sonic window implant when the ledge has been removed and no recessed margin into the cranium has been created as a shelf for seating. Thin cranial fixation plates can be simple bars, x-shaped, or in various shapes conforming to the contour of the cranium to allow the application of multiple titanium screws. For example, if the surgeon wishes to resect a portion or all of a ledge on a sonic window implant, the sonic window implant must be secured to prevent inward or outward displacement resulting from removal of part or all of the ledge. Care must be taken to minimize encroachment by the cranial fixation plate onto the highly polished region of the sonic window. Titanium is highly reflective of ultrasound and can reduce the usable area of the sonic window.

Figure 8A:
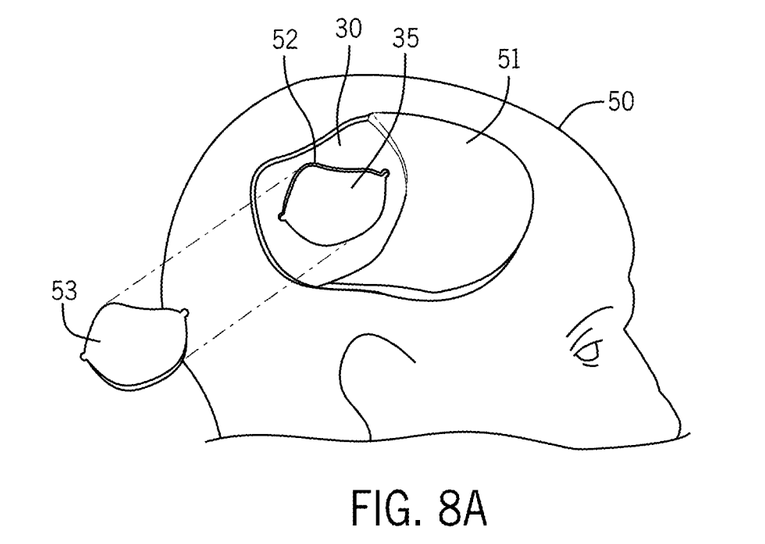
FIG. 8A illustrates a side view of a head of a patient with a portion of the scalp pulled back from the cranium exposing an irregularly shaped surgical opening in the cranium.
Figure 8B:
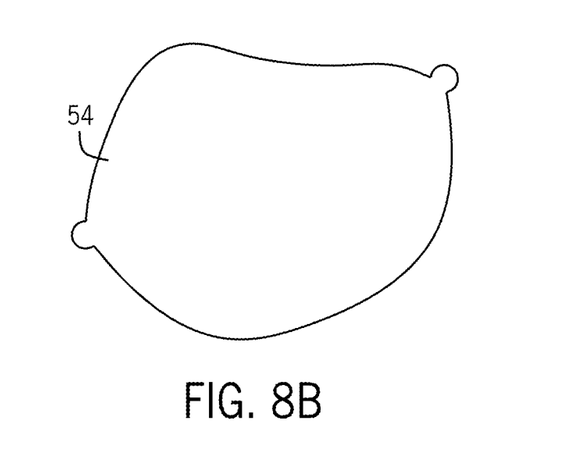
FIG. 8B shows a top view of a customized sonic window implant that is designed with an irregular contour and cranial thickness to fit in the irregularly shaped surgical opening shown in FIG. 8A.

FIG. 8A illustrates the head 50 of a patient with a portion of the scalp 51 pulled back from the cranium 30 exposing an irregularly shaped surgical opening 52 in the cranium 30. A corresponding irregularly shaped piece of resected cranium 53 is removed from the cranium 30. FIG. 8B illustrates a customized sonic window implant 54 that can be designed with an irregular contour and cranial thickness to fit in the irregularly shaped surgical opening 52 shown in FIG. 8A. After the sonic window implant is implanted the scalp is folded over the sonic window implant and onto the cranium. While it is commonly practiced by a neurosurgeon to order a custom cranial replacement from materials such as titanium, polyethylene, or PEEK, the customized sonic window implant requires further characteristics of high-quality ultrasound transmission through the sonic window. The customized sonic window implant can be manufactured from CT scan or MRI bone defect data. In a manufacturing process the customized sonic window implant can be designed to fit the cranial defect precisely, incorporate the highly polished top exterior surface and bottom interior surface, as well as incorporate a lateral ledge with high ultrasound reflectivity borders for localization and manufacturing data. Dural contact to the undersurface or surgical techniques to fill a gap above the dura with saline or conductive gel make the custom sonic window implant immediately usable. Unusual cranial locations are generally used for both surveillances, such as tumor cavity resection, and the application of therapeutic ultrasound modalities, such as opening the blood brain barrier for chemotherapy, thermal ablation, or neuromodulation. A generic highly polished sonic window as described above can be modified to a degree on the surgical field to make it acceptable in unusual alternative cranial locations. The surgeon, when making modifications, must avoid milling or scoring the sonic window surfaces where ultrasound is intended to be used. A standard PEEK customized implant can be modified to incorporate the polished regions for acceptable subjacent imaging and therapeutic delivery to the brain, consistent with the disclosures herein.

Intraoperative guidance systems which render localizing MRI or CT imaging to a target tissue at surgery are known. Simultaneous real time ultrasound through a sonic window can be computationally fused to a preoperative MRI or CT image, allowing compensation for movement of soft tissue, so-called brain warping. Simultaneous use of ultrasound through a sonic window and an intraoperative guidance system provides separate images as well as fused images. Specifically, guidance systems use various tracking mechanisms such as infrared or magnetic field to align an instrument tip with the anatomy of the surgical field, commonly MRI rendered in axial, sagittal, and coronal views or a reconstructed 3-dimensional view. Sometimes other data sets are also employed such a positron emission tomography (PET) scan brain activity or metabolism, CT scan, MEG scan (magnetoencephalography) or EEG (electroencephalography) or vasculature location. All these methods suffer from the disadvantage that they render soft tissue such as brain or scalp or other organs in location only at the time of data acquisition. The brain readily warps or shifts its shape when the cranium is opened or it is retracted, making such preoperative localization inaccurate to varying degrees of significance. On the other hand, ultrasound can be rendered in real time and can be compared to guidance system data to quantify such shape shift as well as precisely compensate for tissue movement during surgical procedures. Ultrasound can also be computationally fused for dimensions to pre-acquired data to more accurately localize a target tissue. The combination of real time ultrasound through a sonic window and pre-procedure imaging from CT, MRI, PET etc. provides a unique opportunity for detecting change and providing new treatment options. For example, a patient in surveillance for recurrence of a brain tumor can be imaged through the sonic window at the same time that the ultrasound instrument has been calibrated to the intraoperative guidance system, even in an outpatient setting.

Figure 9:
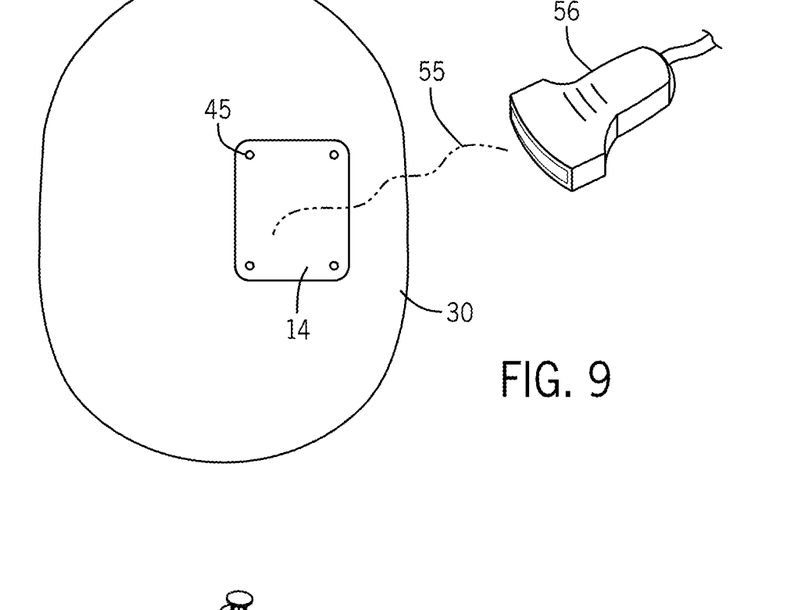
FIG. 9 shows a top view of a cranium with a sonic window and the use of low frequency, high intensity ultrasound from an ultrasound generator through the sonic window.

FIG. 9 shows the use of low frequency, high intensity ultrasound 55 from an ultrasound generator 56 through a sonic window 14 in the cranium 30 to open the blood brain barrier, often in conjunction with an intravenously delivered ultrasound contrast agent (microbubbles) to enable highly focused chemotherapy. Diagnostic ultrasound through a sonic window allows measurement of change and identification of treatment targets. Diagnostic ultrasound can then be converted to therapeutic ultrasound for targeted ablation of tissue, opening of the blood brain barrier for chemotherapy, or neuromodulation. Examples of the neuromodulation include ultrasonic modulation of seizure risk, depression, or pain. Thus, a sonic window enables options of diagnostic and therapeutic management of chronic conditions, such as neoplasms, epilepsy, depression, chronic central pain, and hydrocephalus, by serial ultrasound interventions over time.

Figure 10A:
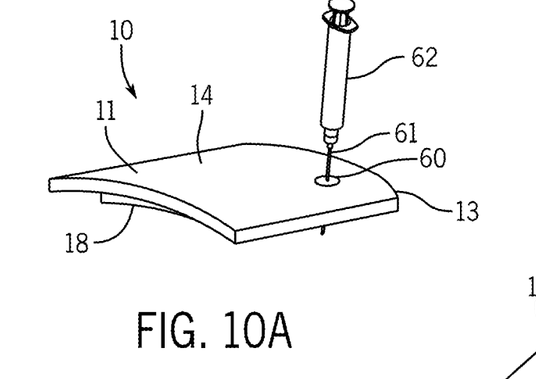
FIG. 10A shows a top perspective view of an elastomer port in a sonic window for applying medicaments or instrument access.
Figure 10B:
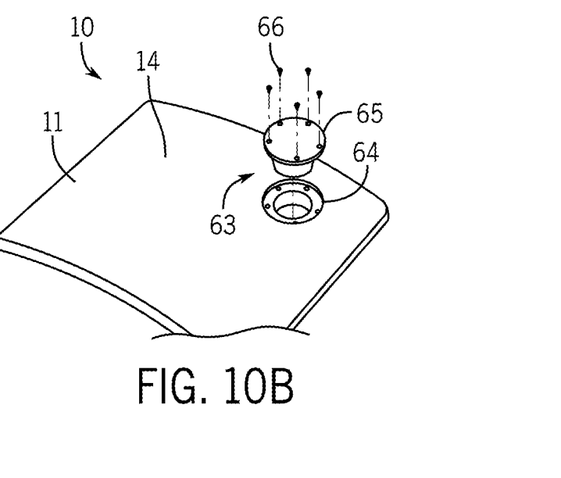
FIG. 10B shows a top perspective view of a plug style port having an opening in a sonic window for applying medicaments or instrument access.

FIG. 10A shows an elastomer port 60 in the sonic window 14 for applying medicaments or instrument access. For example, a hypodermic needle 61 on a syringe 62 can penetrate the elastomer port 60 and contents of the syringe 62 can be injected into the cranial cavity. FIG. 10B shows a plug style port 63 having an opening 64 in the sonic window 14 for applying medicaments or instrument access. A removable plug 65 closes the opening 64 and may be fastened reversibly to the sonic window 14 with screws 66. The removable plug 65 may be made of the same material as the sonic window 14 or it may be made of an elastomer such as silicone that can be perforated with a hypodermic needle 61 for injection of medicaments into the cranial cavity. The perforating needle can commonly have highly reflective etching on its surface at the tip to allow precise guidance to the target under diagnostic ultrasound control. The plug style port 63 port may be used to inject conductive gel or saline to fill a gap above the dura to maintain ultrasound transmission.

The foregoing description illustrates and describes the disclosure. Additionally, the disclosure shows and describes only the preferred embodiments but, as mentioned above, it is to be understood that the preferred embodiments are capable of being formed in various other combinations, modifications, and environments and are capable of changes or modifications within the scope of the invention concepts as expressed herein, commensurate with the above teachings and/or the skill or knowledge of the relevant art.

The embodiments described herein above are further intended to explain the best modes known by applicant and to enable others skilled in the art to utilize the disclosure in such, or other, embodiments and with the various modifications required by the particular applications or uses thereof. Accordingly, the description is not intended to limit the invention to the form disclosed herein. Also, it is intended that the appended claims be construed to include alternative embodiments. It will be further understood that various changes in the details, materials, and arrangements of the parts which have been described and illustrated above in order to explain the nature of this invention may be made by those skilled in the art without departing from the principle and scope of the invention as recited in the following claims.

The invention claimed is:

1. A sonic window implant device, comprising:
   a) a border forming a ledge;
   b) a sonic window within the border, said sonic window being transmissible to ultrasound;
   c) said sonic window having a top exterior surface and a bottom interior surface; and d) an extending portion of said sonic window extending below the ledge, wherein the ledge is reflective of ultrasound for visualization of the border of the sonic window implant device, wherein the sonic window has an access port and wherein said ledge has one or more holes with connecting members, the connecting members configured to be positioned between the cranium and the sonic window when the sonic window implant device is implanted in the cranium, the one or more holes and the connecting members constructed to tent dura mater upward to the bottom interior surface of the sonic window.

2. The sonic window implant device of claim 1, wherein the sonic window implant device is made of polyether ether ketone plastic and the top exterior surface and the bottom interior surface of the sonic window have a polished finish surface at least 16-micron root mean square or less.

3. The sonic window implant device of claim 1, wherein the ledge contains indicia readable through ultrasound.

4. The sonic window implant device of claim 1, further comprising the top exterior surface and the bottom interior surface coated with polytetrafluoro ethylene.

5. The sonic window implant device of claim 1, further comprising the ledge having one or more holes constructed to attach the sonic window implant device to a cranium with screws.

6. The sonic window implant device of claim 1, wherein the access port is an elastomer port.

7. The sonic window implant device of claim 1, further comprising a template of said sonic window for creating an opening in a cranium for implanting the sonic window implant device.

8. The sonic window implant device of claim 1, wherein the access port is a plug port having an opening in the sonic window.

9. The sonic window implant device of claim 1, wherein the ledge is attachable to a recessed bone ledge in an opening in the cranium.

10. A sonic window implant device, comprising:
a) a border forming a ledge;
b) a sonic window within the border, said sonic window being transmissible to ultrasound;
c) said sonic window having a top exterior surface and a bottom interior surface;
d) an extending portion of said sonic window extending below the ledge, wherein the ledge is reflective of ultrasound for visualization of the border of the sonic window implant device, wherein the sonic window implant device is made of polyether ether ketone and the top exterior surface and the bottom interior surface of the sonic window are polished to at least a 16 micron root mean square, wherein the sonic window has an access port and wherein said ledge has one or more holes with connecting members, the connecting members configured to be positioned between the cranium and the sonic window when the sonic window implant device is implanted in the cranium, the one or more holes and the connecting members constructed to tent dura mater upward to the bottom interior surface of the sonic window, and
e) the ledge having one or more holes constructed to attach the sonic window implant to a cranium with screws.

11. The sonic window implant device of claim 10, wherein the access port is an elastomer port.

12. The sonic window implant device of claim 10, wherein the ledge contains indicia readable through ultrasound.

13. The sonic window implant device of claim 10, further comprising the top exterior surface and the bottom interior surface coated with polytetrafluoro ethylene.

14. The sonic window implant device of claim 10, further comprising a template of said sonic window for creating an opening in a cranium for implanting the sonic window implant device.

15. The sonic window implant device of claim 10, wherein the access port is a plug port having an opening in the sonic window.

16. The sonic window implant device of claim 10, wherein the ledge is attachable to a recessed bone ledge in an opening in the cranium.

17. A sonic window implant device, comprising:
a) a border forming a ledge;
b) a sonic window within the border, said sonic window being transmissible to ultrasound;
c) said sonic window having a top exterior surface and a bottom interior surface;
d) an extending portion of said sonic window extending below the ledge;
wherein the top exterior surface and the bottom interior surface are parallel and curved, wherein the ledge is reflective of ultrasound for visualization of the border of the sonic window implant device, wherein the ledge contains indicia readable through ultrasound, wherein the sonic window implant is made of polyether ether ketone and the top exterior surface and the bottom interior surface of the sonic window are polished to at least a 16 micron root mean square, wherein the sonic window has an access port, and wherein said ledge has one or more holes with connecting members, the connecting members configured to be positioned between the cranium and the sonic window when the sonic window implant device is implanted in the cranium, the one or more holes and the connecting members constructed to tent dura mater upward to the bottom interior surface of the sonic window;
e) the ledge having one or more holes constructed to attach the sonic window implant to a cranium with screws; and
f) the top exterior surface and the bottom interior surface are coated with polytetrafluoro ethylene.

18. The sonic window implant device of claim 17, further comprising a template of said sonic window for creating an opening in a cranium for implanting the sonic window implant device.

19. The sonic window implant device of claim 17, wherein the port is an elastomer port or a plug port having an opening in the sonic window.

20. The sonic window implant device of claim 17, wherein the ledge is attachable to a recessed bone ledge in an opening in the cranium.

* * * * *